(12) United States Patent
Galley et al.

(10) Patent No.: US 6,452,001 B2
(45) Date of Patent: Sep. 17, 2002

(54) DIAZAPANE DERIVATIVES USEFUL AS ANTAGONISTS OF NEUROKININ 1 RECEPTOR AND METHODS FOR THEIR FORMATION

(75) Inventors: Guido Galley, Rheinfelden (DE); Annick Goergler, Colmar (FR); Thierry Godel, Basel (CH); Reinhard Heck, Neckargemünd (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/854,885

(22) Filed: May 14, 2001

(30) Foreign Application Priority Data

May 25, 2000 (EP) .......................................... 00111249

(51) Int. Cl.⁷ .................... C07D 243/00; C07D 255/04; C07D 401/00; C07D 223/10; C07D 223/12
(52) U.S. Cl. ...................... 540/492; 540/501; 540/524; 540/526; 540/527
(58) Field of Search ............................... 540/492, 501, 540/524, 526, 527

(56) References Cited

U.S. PATENT DOCUMENTS

| 4,022,765 A | 5/1977 | Wade et al. |
| 5,798,359 A | 8/1998 | Shue et al. |
| 5,972,938 A | 10/1999 | Rupniak et al. ......... 514/236.2 |

FOREIGN PATENT DOCUMENTS

| WO | 95/16679 | 6/1995 |
| WO | 95/18124 | 7/1995 |
| WO | 95/23798 | 9/1995 |

OTHER PUBLICATIONS

Barker, *Reviews in the Neurosciences*, vol. 7,, No. 3, pp. 187–214 (1996).
Longmore et al., *Can. J. Physiol. Pharmacol.*, vol. 75, pp. 612–621 (1997).
Maggi et al., *J. Auton. Pharmacol*, vol. 13, pp. 23–93 (1993).
Navari et al., *The New England Journal of Medicine*, vol. 340, No. 3, pp. 190–195 (1999).
Neuropeptides, vol. 32(1), pp. 1–49 (1998).
Eur. J. Pharmacol., vol. 383(3), pp. 297–303 (1999).

*Primary Examiner*—Bruck Kifle
(74) *Attorney, Agent, or Firm*—George W. Johnston; Patricia S. Rocha-Tramaloni; Arthur D. Dawson

(57) ABSTRACT

The invention relates to compounds of the formula

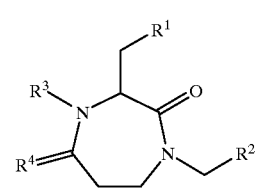

I wherein $R^1$, $R^2$ are independently from each other aryl or heteroaryl, wherein the heteroaryl group contains one or two heteroatoms, selected from N, O, or S, and wherein the aryl or heteroaryl groups are optionally substituted by 1 to 3 substituents, which are independently from each other halogen, $CF_3$, lower alkoxy or lower alkyl;

$R^3$ is hydrogen, lower alkyl, $-(CH_2)_nN(R)_2$, $-(CH_2)_n$-heteroaryl or is a $-(CH_2)_n$-non aromatic heterocycle, which heterocycles are optionally substituted by halogen, $CF_3$, lower alkoxy or lower alkyl;

$R^4$ is $=O$, $=N(CH_2)_nCH_3$ or $=N(CH_2)_nN(R)_2$;

$R^3$ and $R^4$ may be together with the N and C atoms to which they are attached the group $-CR^5=N-N=$; $R^5$ is hydrogen, $-(CH_2)_nN(R)_2$, $-(CH_2)_n$-heteroaryl or is a $-(CH_2)_n$-non aromatic heterocycle, which heterocycles are optionally substituted by halogen, $CF_3$, lower alkoxy or lower alkyl;

R is hydrogen or lower alkyl;

n is 0, 1, 2 or 3;

and pharmaceutically acceptable acid addition salts and enantiomeric forms thereof. The compounds are useful in the treatment of diseases, related to the NK-1 receptor.

61 Claims, No Drawings

DIAZAPANE DERIVATIVES USEFUL AS ANTAGONISTS OF NEUROKININ 1 RECEPTOR AND METHODS FOR THEIR FORMATION

FIELD OF INVENTION

The present invention is generally related to diazapane compounds and more particularly to substituted diazapane compounds showing utility as antagonists of Neurokinin 1 Receptors.

BACKGROUND

The neuropeptide receptors for substance P (NK-1) are widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214) and anxiety (Can., J. Phys., 1997, 75, 612–621).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

Furthermore, neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

NK1 receptor antagonists have been reported to have also a beneficial effect in the therapy of traumatic brain injury (oral disclosure by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimmo, C. J. Bennett, X.Hu, I. Cemak, R. Vink))."

SUMMARY

The present invention provides a compound of the formula

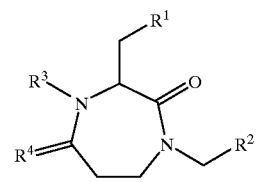

I wherein
- $R^1$, $R^2$ are independently from each other aryl or heteroaryl, wherein the heteroaryl group contains one or two heteroatoms, selected from N, O or S, and wherein the aryl or heteroaryl groups are unsubstituted or substituted by 1 to 3 substituents, which are independently from each other halogen, $CF_3$, lower alkoxy or lower alkyl;
- $R^3$ is hydrogen, lower alkyl, $-(CH_2)_nN(R)_2$, $-(CH_2)_n$-heteroaryl or is a $-(CH_2)_n$-non aromatic heterocycle, the heterocycles are unsubstituted, or substituted by halogen, $CF_3$, lower alkoxy or lower alkyl;
- $R^4$ is $=O$, $=N(CH_2)_nCH_3$ or $=N(CH_2)_nN(R)_2$, or wherein $R^3$ and $R^4$ together with the N and C atoms to which they are attached, form the group $-CR^5=N-N=$;
- $R^5$ is hydrogen, $-(CH_2)_nN(R)_2$, $-(CH_2)_n$-heteroaryl or is a $-(CH_2)_n$-non aromatic heterocycle, which heterocycles are unsubstituted, or, substituted by halogen, $CF_3$, lower alkoxy or lower alkyl;
- R is hydrogen or lower alkyl;
- n is 0, 1, 2 or 3;

and pharmaceutically acceptable acid addition salts and their enantiomers.

The compound of formula I and pharmaceutically acceptable salts thereof are characterized by valuable therapeutic properties. It has been surprisingly found that the compounds of the present invention are antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The compounds of formula I can also be used in form of their prodrugs. Examples are esters, N-oxides, phosphate esters, glycoamide esters, glyceride conjugates and the like. The prodrugs may add to the value of the present compounds advantages in adsorption, pharmacokinetics in distribution and transport to the brain.

Objects of the present invention are the compounds of formula I and pharmaceutically acceptable salts and their enatiomeric forms thereof, the preparation of the above-mentioned compounds, pharmaceutical compositions containing them and their manufacture as well as the use of the above-mentioned compounds in the control or prevention of illnesses, especially of illnesses and disorders of the kind referred to earlier or in the manufacture of corresponding medicaments.

DETAILED DESCRIPTION

The present invention is a compound of the stucture

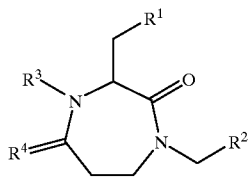

I wherein $R^1$ and $R^2$, are a substituted or unsubstituted aryl ring structure having six to twelve carbon ring atoms, or a substituted or unsubstituted heteroaryl ring structure having five to twelve ring members with one or two of the ring members being a heteroatom selected from the group consisting of nitrogen, oxygen or sulfur. The substituted aryl or heteroaryl ring structure is substituted with one to three substituents selected from the group consisting of halogen, $CF_3$, lower alkoxy, and lower alkyl.

$R^3$ is independently hydrogen, lower alkyl, $-(CH_2)_nN(R)_2$, $-(CH_2)_n-X-$;

$R^4$ is independently $=O$, $=N(CH_2)_nCH_3$ or $=N(CH_2)_nNR_2$, or taken together with $R^3$ and with their respective attached N and C atoms form $-CR^5=N=N-$;

$R^5$ is hydrogen, $-(CH_2)_nN(R)_2$ or is a substituted or unsubstituted $-(CH_2)_n-X$;

X is a substituted or unsubstituted heterocyclic ring structure having five to twelve ring members, with one or two of the ring members being a heteroatom selected from the group consisting of nitrogen, sulfur and oxygen. The substituted heterocyclic ring structure being substituted with one to three substituents selected from the group consisting of halogen, $CF_3$, lower alkoxy, and lower alkyl;

R is hydrogen or lower alkyl; and n is 0, 1, 2 or 3; or a pharmaceutically acceptable salt and enantiomeric forms thereof.

Preferred embodiments of compound I include a compound of structure of I-a

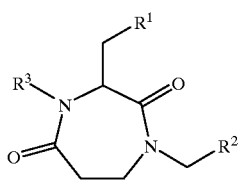

1-a

In one preferred embodiment of compound 1-a, $R^3$ is hydrogen, $R^1$ is an aryl ring structure, such as a substituted phenyl ring structure, and $R^2$ is a substituted ring structure. In another preferred embodiment, $R^3$ and $R^1$ are as above, and $R^2$ is a substituted napthyl ring structure. In yet another preferred embodiment of compound 1-a, $R^1$ is a heteroaromatic ring structure, $R^2$ is a substituted phenyl ring structure and $R^3$ is hydrogen. A further preferred embodiment of compound 1-a includes $R^1$ and $R^2$ as substituted or unsubstituted aromatic ring structures and $R^3$ is a non-aromatic heterocyclic ring structure. Yet another preferred embodiment of compound 1-a has $R^1$ and $R^2$ as substituted or unsubstituted aromatic ring structures, and $R^3$ as an aromatic heterocycle. In a further preferred embodiment of compound 1-a, $R^1$ and $R^2$ are substituted or unsubstituted aromatic ring structures, and $R^3$ is amino alkyl or lower alkyl.

Another preferred embodiment of compound 1 has the structure

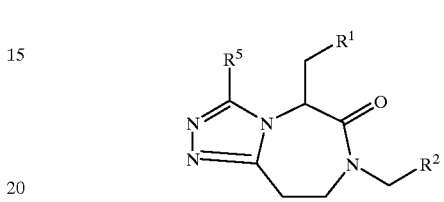

1-b 1-b, wherein $R^1$ and $R^1$ are substituted or unsubstituted ring structures. A preferred embodiment of compound 1-b includes a compound with $R^5$ as hydrogen. Another preferred embodiment of compound 1-b includes $R^5$ as a non-aromatic heterocyclic ring. Yet another preferred embodiment of compound 1-b includes $R^5$ as amino alkyl.

Yet another preferred embodiment of compound 1 has the structure

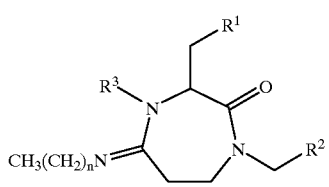

1-c 1-c wherein $R^1$ and $R^2$ are substituted or unsubstituted aromatic ring structures and $R^3$ is hydrogen.

Substance P is a naturally occurring undecapeptide belonging to the tachykinin family of peptides, the latter being so-named because of their prompt contractile action on extravascular smooth muscle tissue. The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "aryl" denotes, for example, phenyl or naphthyl, which may be optionally substituted by one to three substituents, for example by halogen, trifluoromethyl, lower alkyl or lower alkoxy.

The term "heteroaryl" denotes, for example, the following heterocycles: pyridyl, pyrazinyl, pyrimidinyl, pyridazinyl, indazolyl, indolyl, pyrazolyl, benzothienyl, thienyl, furyl, pyrrolyl, imidazolyl, isoquinolyl, isothiazolyl or quinolinyl. Preferred are pyridyl, quinolinyl, indolyl, benzothienyl and pyrazolyl.

The term "non aromatic heterocycle" denotes, for example the following groups: morpholinyl, piperidinyl, pyrrolidinyl, imidazolidinyl, pyrazolidinyl, piperidyl and piperazinyl. Preferred groups are morpholinyl and piperidinyl.

In the reaction schemes below, the symbols 
indicate a solid phase resin such as beta-alanine-$NH_2$-WANG resin and the like.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred are compounds, in which $R^4$ is an oxo group and $R^1$ and $R^2$ are both aryl, for example the following compounds:

(3S)-1-(3,5-bis-trifluoromethyl-benzyl)-3-(3,4-dichloro-benzyl)-[1,4]diazepane-2,5-dione, (3S)-3-(3,4-dichloro-benzyl)-1-(2-methoxy-naphthalen-1-yl-methyl)-[1,4]diazepane-2,5-dione, (3S)-3-(3,4-dichloro-benzyl)-1-(2-methyl-naphthalen-1-yl-methyl)-[1,4]diazepane-2,5-dione, 3-(3,4-dichloro-benzyl)-1-(2-ethoxy-naphthalen-1-yl-methyl)-[1,4]diazepane-2,5-dione, (RS)-1-(3,5-bis-trifluoromethyl-benzyl)-3-(3,4-dichloro-benzyl)-5-propylimino-[1,4]diazepan-2-one hydrochloride and (RS)-3-(3,4-dichloro-benzyl)-1-(2-methoxy-naphthalen-1-yl-methyl)-4-pyridin-3-ylmethyl-[1,4]diazepane-2,5-dione.

Further preferred are compounds, in which $R^4$ is an oxo group and one of $R^1$ or $R^2$ is aryl and the other is heteroaryl. An example of such compound is:

(3S)-3-(1H-indol-3-yl-methyl)-1-(2-methoxy-naphthalen-1-ylmethyl)-[1,4]diazepane-2,5-dione.

Preferred are further compounds, in which $R^4$ is an oxo group and $R^1$ and $R^2$ are both heteroaryl, for example the following compound:

(3S)-1-(2,8-bis-trifluoromethyl-quinolin-4-yl-methyl)-3-(1H-indol-3-ylmethyl)-[1,4]diazepane-2,5-dione.

Further preferred are compounds, in which $R^3$ and $R^4$ are together with the N and C atom to which they are attached the group —$CR^5$=N—N= and $R^5$ has the meaning described above.

Examples of such compounds are:

(4S)-4-(3,4-dichloro-benzyl)-6-(2-methoxy-naphthalen-1-yl-methyl)-7,8-dihydro-6H-1,2,3a,6-tetraaza-azulen-5-one, (RS)-6-(3,5-bis-trifluoromethyl-benzyl)-4-(3,4-dichloro-benzyl)-7,8-dihydro-6H-1,2,3a,6-tetraaza-azulen-5-one, (RS)-6-(3,5-bis-trifluoromethyl-benzyl)-4-(3,4-dichloro-benzyl)-3-(2-morpholin-4-yl-ethyl)-7,8-dihydro-6H-1,2,3a,6-tetraaza-azulen-5-one, (RS)-6-(3,5-bis-trifluoromethyl-benzyl)-4-(3,4-dichloro-benzyl)-3-piperidin-1-yl-methyl-7,8-dihydro-6H-1,2,3a,6-tetraaza-azulen-5-one, (RS)-6-(3,5-bis-trifluoromethyl-benzyl)-4-(3,4-dichloro-benzyl)-3-dimethylaminomethyl-7,8-dihydro-6H-1,2,3a,6-tetraaza-azulen-5-one, (RS)-6-(3,5-bis-trifluoromethyl-benzyl)-4-(3,4-dichloro-benzyl)-3-(1-methyl-piperidin-2-yl)-7,8-dihydro-6H-1,2,3a,6-tetraaza-azulen-5-one and (RS)-4-(3,4-dichloro-benzyl)-6-naphthalen-1-yl-methyl-7,8-dihydro-6H-1,2,3a,6-tetraaza-azulen-5-one.

The present compounds of formula I and their pharmaceutically acceptable salts can be prepared by methods known in the art, for example, by processes described below, which process comprises a) cyclizing a compound of formula

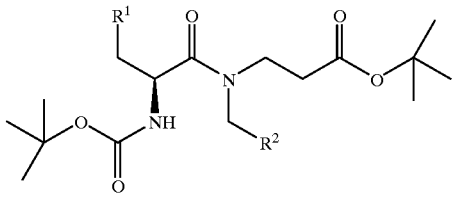

XIV to give a compound of formula

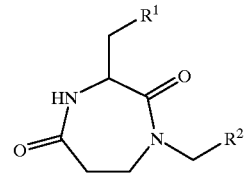

I-1 wherein $R^1$ and $R^2$ have the significances given above, or reacting a compound of formula

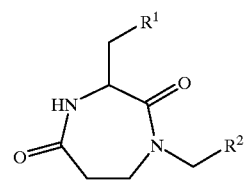

I-1 with a compound of formula $R^3$—X    II to a compound of formula

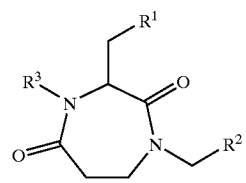

I-2 wherein $R^1$ to $R^3$ have the significances given above and X is halogen, or cyclizing a compound of formula

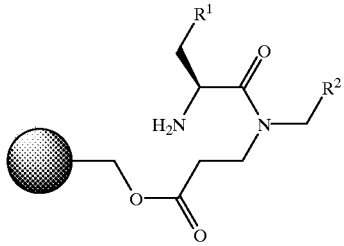

III to give a compound of formula

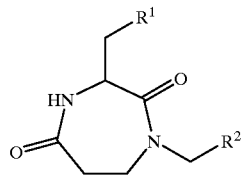

I-1 wherein $R^1$ and $R^2$ have the significances given above, or reacting a compound of formula

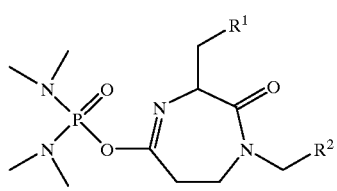

IV with a compound of formula $R^6$—$NH_2$  V to a compound of formula

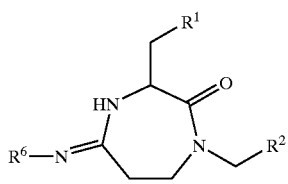

I-3 wherein $R^6$ is —$(CH_2)_nCH_3$ or —$(CH_2)_nN(R)_2$ and $R^1$, $R^2$, n and R are given above, or reacting a compound of formula

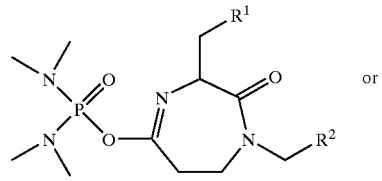

IV or

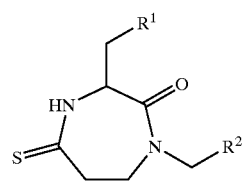

XX with a compound of formula $R^5$—CO·N—$NH_2$  VI to a compound of formula

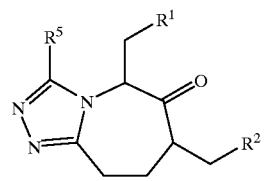

I-4 wherein the definitions of substituents are given above, or cyclizing a compound of formula

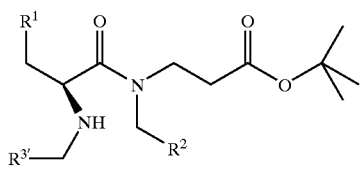

VII to a compound of formula

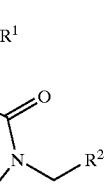

I-5 wherein $R^{3'}$ is lower alkyl, —$(CH_2)_{n-1}N(R)_2$, —$(CH_2)_{n-1}$-heteroaryl or is a —$(CH_2)_{n-1}$-non aromatic heterocycle, which heterocycles are optionally substituted by halogen, $CF_3$, lower alkoxy or lower alkyl; and $R^1$ and $R^2$ are described above, or modifying one or more substituents $R^1$-$R^3$ within the definitions given above, and if desired, converting the compound obtained into a pharmaceutically acceptable acid addition salt or into its enantiomeric form.

The following schemes 1–4 describe the processes for preparation of compounds of formula I in more detail. The starting materials are known compounds or may be prepared according to methods known in the art.

In the schemes the following abbreviations have been used:

BOP-Cl bis-(2-oxo-3-oxazolidinyl)phosphinic chloride
DDC N-(3-dimethylaminopropyl)-N'-ethylcarbodiimide
NMM N-methylmorpholine
DIPEA N-ethyldiisopropyl-amine
TFA trifluoroacetic acid
HOBT 1-hydroxy-benzotriazole
DIC diisopropylcarbodiimide
Fmoc [(9H-fluoren-9-ylmethoxy)carbonyl]
HOAt 1-hydroxy-7-azabenzotriazole

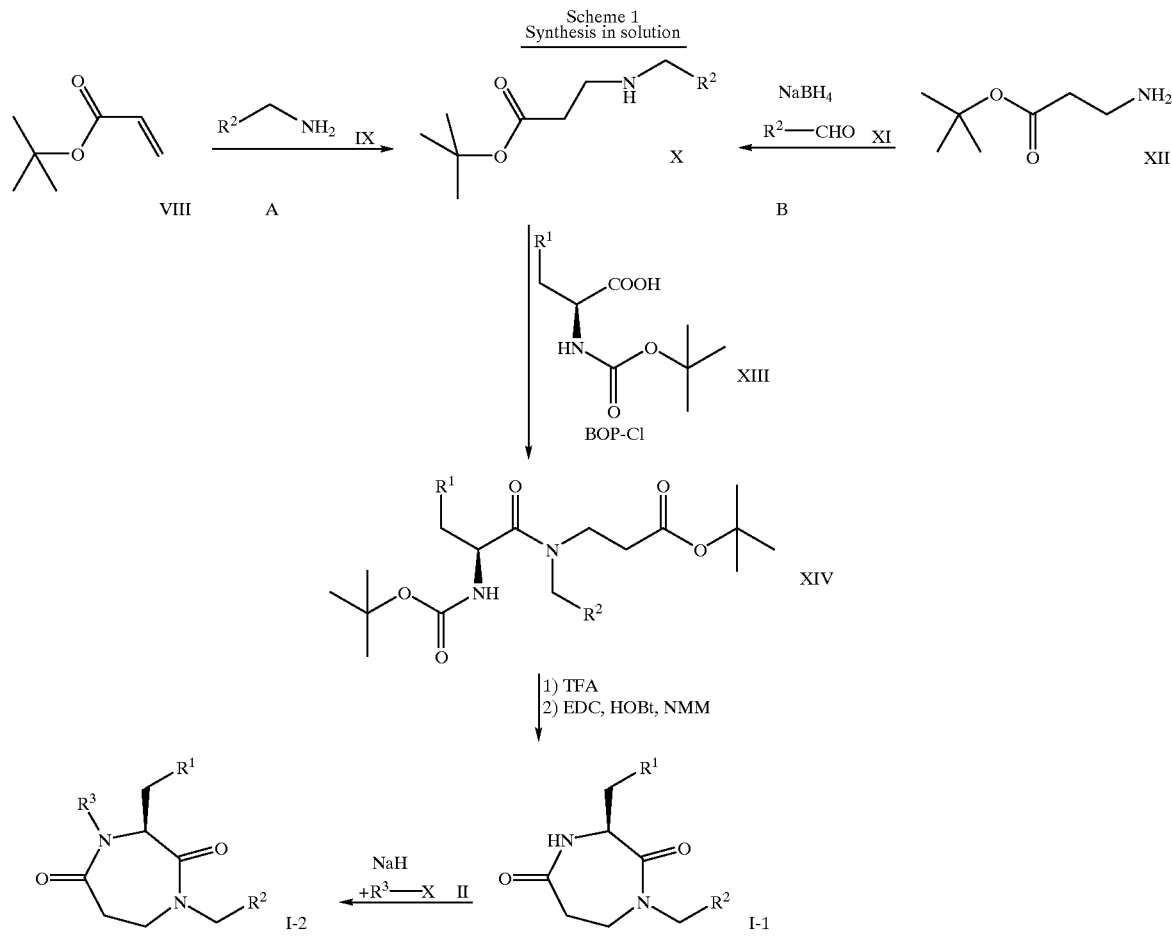

The definition of substituents is described above.

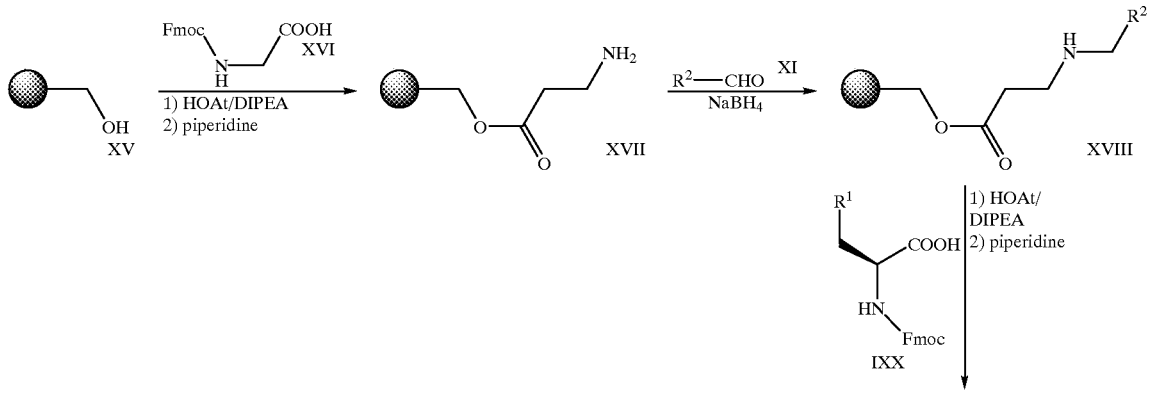

-continued
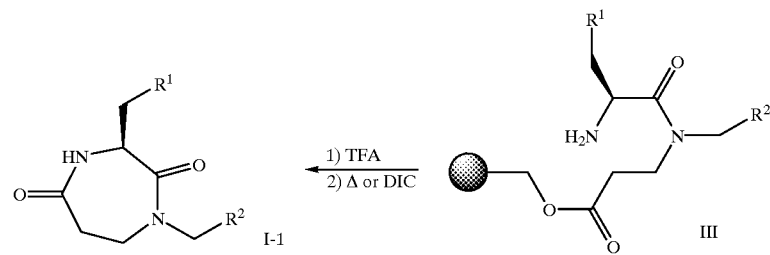
The substituents are described above.
Scheme 3
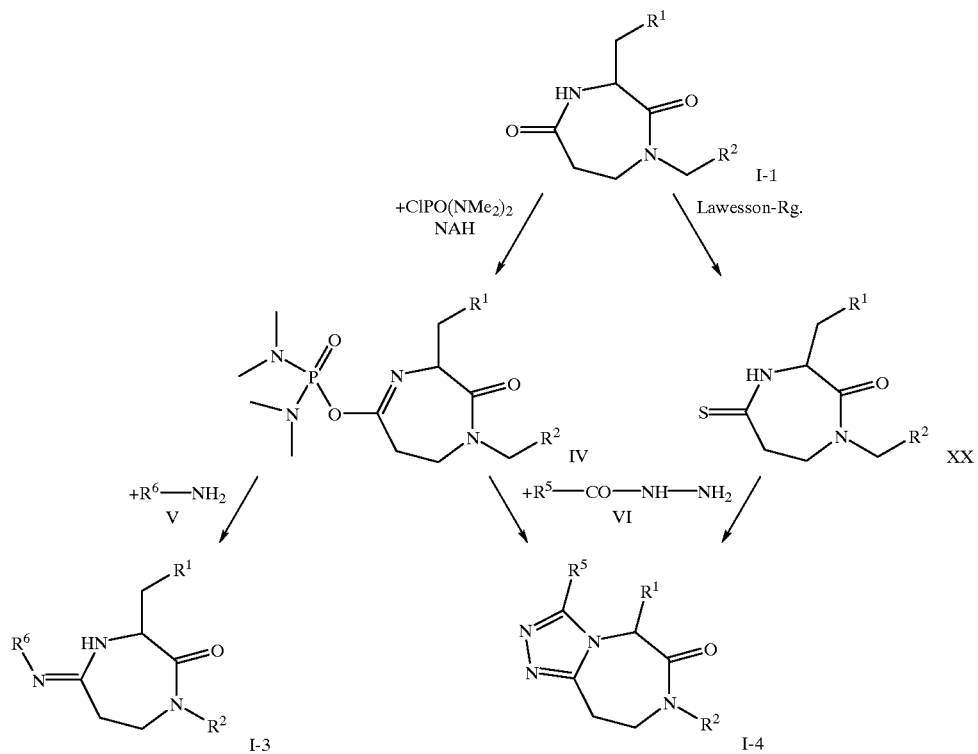
$R^1$, $R^2$ and $R^5$ are described above and $R^6$ is —$(CH_2)_nCH_3$ or —$(CH_2)_nN(R)_2$ and R is hydrogen or lower alkyl and n is 0 to 3.
Scheme 4
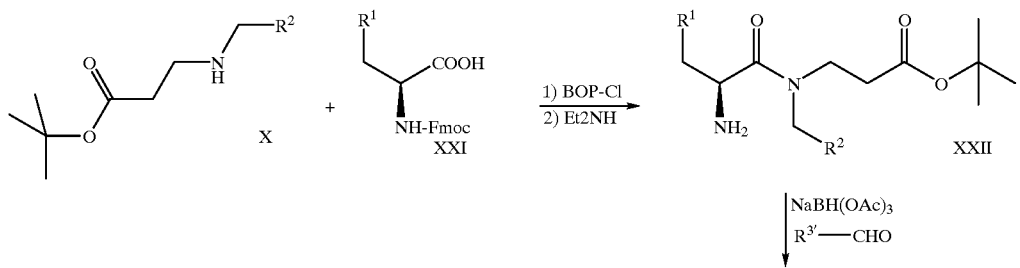

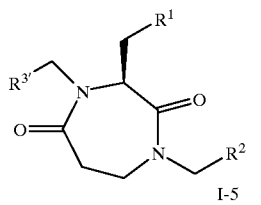 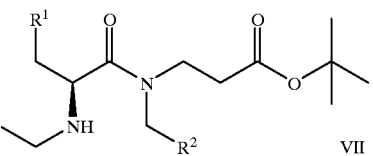

R¹ and R² are described above and R³' is lower alkyl, —$(CH_2)_{n-1}N(R)_2$, —$(CH_2)_{n-1}$-heteroaryl or is a —$(CH_2)_{n-1}$-non aromatic heterocycle, which heterocycles are optionally substituted by halogen, $CF_3$, lower alkoxy or lower alkyl;

In accordance with scheme 1 compounds of examples 1 to 5 and 8 to 18 have been prepared as follows:

A compound of formula IX, wherein R² is, for example, 3,5-trifluoromethylphenyl, naphthalen-1-yl, 4-chloro-3-(trifluoromethyl)-phenyl, 2-methoxy-naphthalen-1-yl, 2-methyl-naphthalen-1-yl or 2-ethoxy-naphthalen-1-yl, is added to an ethanolic solution of tert.-butylacrylate of formula VIII at about 70° C. The obtained liquid is further solved in a solution, containing a compound of formula XIII, wherein R¹ may be, for example 3,4-dichlorophenyl, benzo[b]thiophen-3-yl, 4-chlorophenyl, 3-chlorophenyl, indol-3-yl or 2,4,5-trichloro-phenyl, and N-methylmorpholine (NMM) and bis-(2-oxo-3-oxazolidinyl)phosphinic chloride (BOP-Cl) in dichloromethane. The mixture is stirred for about 2 h at room temperature. After drying, to the residue is added NMM, N-(3-dimethylaminopropyl)-N'-ethylcarbodiimide (EDC), 1-hydroxy-benzotriazole ((HOBT) and N-(3-dimethylaminopropyl)-N'-ethylcarbodiimide (EDC) to obtain a compound of formula I-1.

Further in accordance with scheme 1, the hydrogen atom of compounds of formula I-1 may be replaced by the substituent R³, which process is described in examples 13 and 14 as follows: To a solution of a compound of formula I-1 in DMF is added a sodium hydride suspension in mineral oil at room temperature under argon. Then, a compound of formula II, for example methyliodide or 4-(2-chloroethyl)-morpholine is added to obtain a compound of formula I-2.

In accordance with scheme 1, a compound of formula X may further be obtained by processes, described in examples 2a, 3 and 8. A compound of formula XI, for example 2-methoxynaphthaldehyde, 2,8-bis(trifluoromethyl)-4-quinoline carboxaldehyde or 4-methoxynaphthaldehyde is solved in dichloromethane. To the cooled (0° C.) solution is added sodium borohydride and it is stirred for about 1 h. The residue is purified to give a compound of formula X.

In accordance with scheme 2, examples 6 and 7 are prepared. These processes are solid phase synthesis. A slurry of beta-alanine—$NH_2$—WANG resin in dichloromethane is treated with a compound of formula XI, for example with 1-naphthyldehyde or with bis-3,5-trifluoromethyl-benzylaldehyde, and with sodium triacetatoxyborohydride. The resin is washed with tetrahydrofurane, water, aqueous 10% sodium hydrogencarbonate solution and dichloromethane. A slurry of this resin is allowed to swell to about 30 min. Then 1-hydroxy-7-azabenzotriazole, diisopropylcarbodiimide (DIC), N[(9H-fluoren-9-ylmethoxy)carbonyl]-L-triptophan (Fmoc-L-triptophan) and diisopropylethylamine are added. After the resin was washed, the N-protecting group is removed by adding a solution of piperidine in dimethylformamide at room temperatur. Then the resin is stirred for about 30 min in a mixture of trifluoroacetic acid (TFA) and dichloromethane. After concentration of the organic layers and an azeotropical dry, diisopropylethylamine (DIPEA), DIC and 4-dimethylamine-pyridine are added. The mixture is stirred and the volatiles are removed. A compound of formule I-1 is obtained.

Scheme 3 describes the preparation of compounds of formula I-3 and I-4, specifically described in examples 19 to 27. In accordance with scheme 3, a compound of formula I-1, for example (3S)-3-(3,4-dichloro-benzyl)-1-(2-methoxy-naphthalen-1-ylmethyl)-[1,4]diazepan-2,5-dione, (RS)-1-(3,5-bis-trifluoromethyl-benzyl)-3-(3,4-dichloro-benzyl)-[1,4]diazepan-2,5-dione or (RS)-3-(3,4-dichloro-benzyl)-1-(naphthalen-1-ylmethyl)-[1,4]diazepan-2,5-dione, is solved in dimethylformamide and then a suspension of sodium hydride in mineral oil is added at room temperature. After forming a clear solution, bis(dimethylamino)phosphorochloridate (IV) is added. The reaction mixture is stirred and then a corresponding hydrazine of formula VI is added to give a compound of formula I-4.

An alternative method to obtain a compound of formula I-4 is the reaction of a compound of formula I-1 with the Lawesson's reagent. Lawesson's reagent is 2,4-bis(4-methoxyphenyl)-1,3,2,4-dithiadiphosphetane-2,4-disulphide. The obtained dithioamide was separated by column chromatography and the corresponding hydrazide is added as described above to obtain the desired compound of formula I-4.

Further, in accordance with scheme 3, a compound of formula I-3 is obtained by reacting a compound of formula IV with an amine derivative of formula V. R⁶ in formula V are —$(CH_2)_nCH_3$ or the group —$(CH_2)_nN(R)_2$ and R is lower alkyl or hydrogen and n is 0 to 3. The reaction is carried out at about 50° C.

In accordance with reaction scheme 4 a compound of formula I-5 is obtained. The process steps are described in more detail in examples 28 to 36. A compound of formula XXI, for example 9-fluoremethyloxycarbonyl-L-3,4-dichlorophenylalanine is suspended in a solution of dichloromethane, NMM and BOP-Cl. Then a compound of formula X, for example 3-(3,5-bis-trifluoromethylbenzylamino)-propionic acid tert.-butyl ester is added to give a compound of formula XXII. To a solution of a compound of formula XXII in 1,2-dichloroethane is added a corresponding aldehyde in the presence of sodium triacetoxy-borohydride to give a compound of formula VII, which is then cyclized with TFA, NMM, EDC and HOBT to the corresponding compounds of formula I-5.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter. All of the compounds listed as examples below were active in the following assay. Substance P is a naturally occurring undecapeptide belonging to the tachykinin family of peptides, the latter being so-named because of their prompt contractile action on extravascular smooth muscle tissue.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04 %) leupeptin (8 µg/ml), $MnCl_2$ (3 mM) and phosphoramidon (2 µM). Binding assays consisted of 250 µl of membrane suspension (1.25×10$^5$ cells/assay tube), 0.125 µl of buffer of displacing agent and 125 µl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3 %) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.00–9.00 for the preferred compounds.

In the table below are shown some specific activity data of preferred compounds:

| Example No. | pKi |
| --- | --- |
| 26 | 8.15 |
| 24 | 8.25 |
| 17 | 8.27 |
| 23 | 8.36 |
| 21 | 8.41 |
| 16 | 8.42 |
| 15 | 8.49 |
| 20 | 8.61 |
| 19 | 8.76 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius.

EXAMPLE 1

(3S)-1-(3,5-Bis-trifluoromethyl-benzyl)-3-(3,4-dichloro-benzyl)-[1,4]diazepane-2,5-dione 3-(3,5-Bis-trifluoromethyl-benzylamino)-propionic acid tert-butyl ester To a solution of 641 mg (5 mmol) tert.-butyl acrylate in ethanol 1.22 g (5 mmol) bis-3,5-trifluoromethyl-benzylamine was added. After stirring the solution at 70° C. for 24 h the solvent was evaporated and the residue was purified by flash chromatography (SiO$_2$, petrolether/ether= 1:1) to give 1.255 g (67.5%) of the title compound as colourless liquid.

MS m/e (%): 372.2 (M+H$^+$, 50), 316.2 (M-C$_4$H$_7$).

S-3-[(3,5-Bis-trifluoromethyl-benzyl)-(2-tert-butoxycarbonylamino-3-(3,4-dichlorophenyl)-propionyl)-amino]-propionic acid tert-butyl ester To a solution of 335 mg (1 mmol) tert-butoxycarbonyl-L-3,4-dichlorophenylalanine in 5 ml of dichloromethane 202 mg (2 mmol) N-methylmorpholine and 255 mg (1 mmol) bis(2-oxo-3-oxazolidinyl)phosphinic chloride were added and the mixture was stirred for 15 min at room temperature under argon. Then 371 mg (1 mmol) 3-(3,5-bis-trifluoromethyl-benzylamino)-propionic acid tert-butyl ester was added and the mixture was stirred for 2 h at room temperature. Water (5 ml) was added, the organic layer was separated and the aqueous layer was extracted two times with dichloromethane. The combined organic layers were dried and evaporated. The residue was purified by column chromatography (SiO$_2$, petrolether/ether=1 1) to yield 454 mg (66%) of the title compound.

MS m/e (%): 688 (M+H$^+$, 100), 690 (M+H$^+$, 40).

(3S)-1-(3,5-Bis-trifluoromethyl-benzyl)-3-(3,4-dichloro-benzyl)-[1,4]diazepane-2,5-dione To a solution of 344 mg (0.5 mmol) S-3-[(3,5-bis-trifluoromethyl-benzyl)-(2-tert-butoxycarbonylamino-3-(3, 4-dichlorophenyl)-propionyl)-amino]-propionic acid tert-butyl ester in 2 ml of dichloromethane 2 ml of trifluoroacetic acid were added and the mixture was stirred for 2 hours at room temperature. The solvent and the trifluoroacetic acid were evaporated at reduced pressure. After drying under vacuum the residue was dissolved in 3 ml of dichloromethane and 177 mg (1.75 mmol) N-methylmorpholine, 96 mg (0.5 mmol) N-(3-dimethylaminopropyl)-N'-ethylcarbodiimide hydrochloride and 67 mg (0.5 mmol) 1-hydroxybenzotriazole were added. The mixture was stirred overnight at room temperature. Water (3 ml) was added to the reaction mixture, the two phases were separated and the organic layer was dried over magnesium sulphate. After evaporation of the solvent the residue was purified by column chromatography ($SiO_2$, ethyl acetate) to give 80 mg (43%) of the title compound as a white solid.

MS m/e (%): 554.1 (M+$CH_3$CN+$H^+$, 100), 556.2 (M+$CH_3$CN+$H^+$, 60).

EXAMPLE 2

(3S)-3-(1H-Indol-3-yl-methyl)-1-(2-methoxy-naphthalen-1-yl-methyl)-[1,4]diazepane-2,5-dione 3-[(2-Methoxy-naphthalen-1-yl-methyl)-amino]-propionic acid tert-butyl ester To a solution of 0.559 g (3 mmol) 2-methoxynaphthaldehyde and 0.436 g (3 mmol) 3-aminopropionic acid tert-butyl ester in 6 ml of dichloromethane magnesium sulphate was added and the mixture was shaken for 18 h at room temperature. Magnesium sulphate was separated from the reaction mixture and washed two times with dichloromethane. After evaporating the combined organic layers the residue was re-dissolved in methanol. To the stirred and cooled (0° C.) solution 227 mg (6 mmol) sodium borohydride was added in small portions. Stirring was continued for 1 h at 0° C. Methanol was evaporated, water (50 ml) was added and the mixture was extracted three times with ethyl acetate. The combined organic layers were dried ($MgSO_4$) and concentrated under reduced pressure. The residue was purified by column chromatography ($SiO_2$, petrolether/ether=1:1) to yield 297 mg (31%) of the title compound.

MS m/e (%): 316.3 (M+$H^+$, 100).

S-3-{2-tert-Butoxycarbonylamino-2-[(2-tert-butoxycarbonyl-ethyl)-(2-methoxynaphthalen-1-yl-methyl)-carbamoyl]-ethyl}-indole-1-carboxylic acid tert-butyl ester To a solution of 404 mg (1 mmol) N,1-bis (tert-butoxycarbonyl)-L-tryptophan in 5 ml of dichloromethane 202 mg (2 mmol) N-methylmorpholine and 255 mg (1 mmol) bis(2-oxo-3-oxazolidinyl)phosphinic chloride were added and the mixture was stirred for 15 min at room temperature under argon. Then 315 mg (1 mmol) 3-[(2-methoxy-naphthalen-1-ylmethyl)-amino]-propionic acid tert-butyl ester was added and the mixture was stirred for 2 h at room temperature. Water (5 ml) was added, the organic layer was separated and the aqueous layer was extracted two times with dichloromethane. The combined organic layers were dried and evaporated. The residue was purified by column chromatography ($SiO_2$, petrolether/ether=1:1) to yield 454 mg (66%) of the title compound.

MS m/e (%): 702.4 (M+$H^+$, 100).

(3S)-3-(1H-Indol-3-yl-methyl)-1-(2-methoxy-naphthalen-1-yl-methyl)-[1,4]diazepane-2,5-dione To a solution of 351 mg (0.5 mmol) S-3-{2-tert-butoxycarbonylamino-2-[(2-tert-butoxycarbonyl-ethyl)-(2-methoxynaphthalen-1-ylmethyl)-carbamoyl]-ethyl}-indole-1-carboxylic acid tert-butyl ester in 1 ml of dichloromethane 1 ml of trifluoroacetic acid were added and the mixture was stirred for 2 hours at room temperature. The solvent and the trifluoroacetic acid were evaporated at reduced pressure and a bath temperature of 40° C. After drying under vacuum the residue was dissolved in 3 ml of dichloromethane and 177 mg (1.75 mmol) N-methylmorpholine, 96 mg (0.5 mmol) N-(3-dimethylaminopropyl)-N'-ethylcarbodiimide hydrochloride and 67 mg (0.5 mmol) 1-hydroxybenzotriazole were added. The mixture was stirred overnight at room temperature. Water (3 ml) was added to the reaction mixture, the two phases were separated and the organic layer was dried over magnesium sulphate. After evaporation of the solvent the residue was purified by column chromatography ($SiO_2$, ethyl acetate) to give 50 mg (46%) of the title compound as a white solid.

MS m/e (%): 428.6 (M+$H^+$, 100), 450.4 (M+$Na^+$, 60).

EXAMPLE 3

(3S)-1-(2,8-Bis-trifluoromethyl-quinolin-4-yl-methyl)-3-(1H-indol-3-yl-methyl)-[1,4]diazepane-2, 5-dione The title compound was obtained in comparable yields according to the procedures described for example 2 using 2,8-bis(trifluoromethyl)-4-quinolinecarboxaldehyde instead of 2-methoxynaphthaldehyde in step a).

MS m/e (%): 535.3 (M+$H^+$, 100).

EXAMPLE 4

(RS)-3-(3,4-Dichloro-benzyl)-1-naphthalen-1-yl-methyl-[1,4]diazepane-2,5-dione

The title compound was obtained in comparable yields according to the procedures described for example 1 using 1-aminomethylnaphthaline instead of bis-3,5-trifluoromethyl-benzylamine in step a) and tert-butoxycarbonyl-DL-3,4-dichlorophenylalanine instead of tert-butoxycarbonyl-L-3,4-dichlorophenylalanine in step b).

MS m/e (%): 427.4 (M+$H^+$, 100), 429.4 (M+$H^+$, 50).

EXAMPLE 5

(3S)-3-(3,4-Dichloro-benzyl)-1-naphthalen-1-yl-methyl-[1,4]diazepane-2,5-dione

The title compound was obtained in comparable yields according to the procedures described for example 4 using tert-butoxycarbonyl-L-3,4-dichlorophenyl-alanine instead of tert-butoxycarbonyl-DL-3,4-dichlorophenylalanine in step b).

The compound was determined to be enantiomerically pure (>99%) by chiral HPLC using a CHIRALPAK AS 180 column and the racemic (RS)-3-(3,4-dichloro-benzyl)-1-naphthalen-1-ylmethyl-[1,4]diazepane-2,5-dione (see example 4) as standard.

MS m/e (%): 427.4 (M+$H^+$, 100), 429.4 (M+$H^+$, 60).

EXAMPLE 6

(3S)-3-(1H-Indol-3-yl-methyl)-1-naphthalen-1-yl-methyl-[1,4]diazepane-2,5-dione

A slurry of 1.73 g (2 mmol, loading 0.86 g) beta-alanine-NH2-WANG resin in 50 ml dichloromethane was treated with 2.5 g (16 mmol) 1-naphthaldehyde and 3.4 g (16 mmol) sodium triacetoxyborohydride. After shaking the mixture for 18 h at room temperature the resin was washed successively with tetrahydrofurane, water, aqueous 10% sodium hydrogencarbonate solution, water, tetrahydrofurane, dichloromethane, and dried to yield 1.91 g of a pale yellow resin.

A slurry of this resin in a mixture of 45 ml dichloromethane and 15 ml dimethylformamide was allowed to swell to 30 min. Then 0.82 g (6 mmol) 1-hydroxy-7- azabenzotriazole, 0.76 g (6 mmol) diisopropylcarbodiimide, 2.3 g (6 mmol) N-[(9H-fluoren-9-ylmethoxy)carbonyl]-L-tryptophan and 1.5 g (12 mmol) diisopropylethylamine were added. After shaking for 24 hours the resin was washed with dimethylformamide, dichloromethane, methanol, ether, and dried. To remove the N-protecting group the resin was stirred in 40% solution of piperidine in dimethylformamide (70 ml) at room temperature. The resin was washed with dimethylformamide, methanol, ether, and dried to yield 1.75 g of an off-white resin.

This resin was stirred for 30 min in a mixture of 10 ml trifluoroacetic acid and 10 ml dichloromethane at room temperature. The resin was separated from the solution and washed three times with dichloromethane. The combined organic layers were concentrated under reduced pressure. The residue was dried azeotropically with toluene to yield 0.36 g (45%) of a foamy product.

To a solution of 50 mg (0.12 mmol) of this residue 0.042 ml (0.24 mmol) diisopropylethylamine, 0.038 ml (0.24 mmol) diisopropylcarbodiimide and 2 mg of 4-dimethylamino-pyridine were added. After stirring the mixture for 18 h at room temperature the volatiles were removed, 15% aqueous ammonium chloride solution was added and the mixture was extracted three times with dichloromethane. The combined organic layers were dried over sodium sulphate and concentrated under reduced pressure to yield 43 mg (90%) of an off-white solid.

MS m/e (%): 398.4 (M+H$^+$, 100).

EXAMPLE 7

(3S)-1-(3,5-Bis-trifluoromethyl-benzyl)-3-(1H-indol-3-yl-methyl)-[1,4]diazepane-2,5-dione The title compound was obtained in comparable yields according to the procedures described for example 6 using bis-3,5-trifluoromethyl-benzylaldehyde instead of 1-naphthaldehyde.

MS m/e (%): 484.4 (M+H$^+$, 100).

EXAMPLE 8

(3S)-3-(1H-Indol-3-yl-methyl)-1-(4-methoxy-naphthalen-1-yl-methyl)-[1,4]diazepane-2,5-dione The title compound was obtained in comparable yields according to the procedures described for example 2 using 4-methoxynaphthaldehyde instead 2-methoxynaphthaldehyde in step a).

MS m/e (%): 428.5 (M+H$^+$, 100), 450.4 (M+Na$^+$, 50).

EXAMPLE 9

(3S)-3-Benzo[b]thiophen-3-yl-methyl-1-naphthalen-1-yl-methyl-[1,4]diazepane-2,5-dione The title compound was obtained in comparable yields according to the procedures described for example 1 using 1-aminomethylnaphthaline instead of bis-3,5-trifluoromethyl-benzylamine in step a) and tert-butoxycarbonyl-L-3-benzothienylalanine instead of tert-butoxycarbonyl-L-3,4-dichlorophenylalanine in step b).

MS m/e (%): 415.3 (M+H$^+$, 100), 437.4 (M+Na$^+$, 70).

EXAMPLE 10

(3S)-3-(4-Chloro-benzyl)-1-naphthalen-1-yl-methyl-[1,4]diazepane-2,5-dione

The title compound was obtained in comparable yields according to the procedures described for example 1 using 1-aminomethylnaphthaline instead of bis-3,5-trifluoromethyl-benzylamine in step a) and tert-butoxycarbonyl-L-4-chlorophenylalanine instead of tert-butoxycarbonyl-L-3,4-dichlorophenylalanine in step b).

MS m/e (%): 393.2 (M+H$^+$, 100), 395.2 (M+H$^+$, 60).

EXAMPLE 11

(3S)-3-(3-Chloro-benzyl)-1-naphthalen-1-yl-methyl-[1,4]diazepane-2,5-dione

The title compound was obtained in comparable yields according to the procedures described for example 1 using 1-aminomethylnaphthaline instead of bis-3,5-trifluoromethyl-benzylamine in step a) and tert-butoxycarbonyl-L-3-chlorophenylalanine instead of tert-butoxycarbonyl-L-3,4-dichlorophenylalanine in step b).

MS m/e (%): 393.2 (M+H$^+$, 100), 395.2 (M+H$^+$, 50).

EXAMPLE 12

(3S)-1-(4-Chloro-3-trifluoromethyl-benzyl)-3-(1H-indol-3-yl-methyl)-[1,4]diazepane-2,5-dione The title compound was obtained in comparable yields according to the procedures described for example 1 using 4-chloro-3-(trifluoromethyl)-benzylamine instead of bis-3,5-trifluoromethyl-benzylamine in step a) and N,1-bis(tert-butoxycarbonyl)-L-tryptophan instead of tert-butoxycarbonyl-L-3,4-dichlorophenylalanine in step b).

MS m/e (%): 450.3 (M+H$^+$, 100) 452.2 (M+H$^+$, 30).

EXAMPLE 13

(RS)-3-(3,4-Dichloro-benzyl)-4-methyl-1-naphthalen-1-yl-methyl-[1,4]diazepane-2,5-dione To a solution of 214 mg (0.5 mmol) (RS)-3-(3,4-dichloro-benzyl)-1-naphthalen-1-ylmethyl-[1,4]diazepane-2,5-dione in 3 ml dimethylformamide 26 mg (0.6 mmol) of a 55% sodium hydride suspension in mineral oil was added at room temperature under argon. After a clear solution was formed (within about 20 min) 106 mg (0.75 mmol) of methyliodide was added. The reaction mixture was stirred at room temperature under argon overnight. After evaporation of the solvent in vacuum water (5 ml) was added and the mixture was extracted three times with ethyl acetate. The combined organic layers are dried (MgSO$_4$) and concentrated. The residue was purified by column chromatography (SiO$_2$, ethyl acetate) to yield 129 mg (58.5%) of the title compound as white crystals.

MS m/e (%): 441.3 (M+H$^+$, 100) 443.3 (M+H$^+$, 50).

EXAMPLE 14

(RS)-3-(3,4-Dichloro-benzyl)-4-(2-morpholin-4-yl-ethyl)-1-naphthalen-1-yl-methyl-[1,4]diazepane-2,5-dione hydrochloride The title compound was obtained in comparable yields according to the procedures described for example 13 using 4-(2-chloroethyl)-morpholine together with a catalytical amount of potassium iodide instead of methyliodide followed by formation of the hydrochloric salt.

MS m/e (%): 540.3 (M+H$^+$, 100), 542.3 (M+H$^+$, 70).

EXAMPLE 15

(3S)-3-(3,4-Dichloro-benzyl)-1-(2-methoxy-naphthalen-1-yl-methyl)-[1,4]diazepane-2,5-dione The title compound was obtained in comparable yields according to the procedures described for example 1 using 1-aminomethyl-2-methoxy-naphthaline instead of bis-3,5-trifluoromethyl-benzylamine in step a).

MS m/e (%): 457.4 (M+H$^+$, 100).

EXAMPLE 16

(3S)-3-(3,4-Dichloro-benzyl)-1-(2-methyl-naphthalen-1-yl-methyl)-[1,4]diazepane-2,5-dione The title compound was obtained in comparable yields according to the procedures described for example 1 using 1-aminomethyl-2-methyl-naphthaline instead of bis-3,5-trifluoromethyl-benzylamine in step a).

MS m/e (%): 441.4 (M+H$^+$, 100).

EXAMPLE 17

(RS)-3-(3,4-Dichloro-benzyl)-1-(2-ethoxy-naphthalen-1-yl-methyl)-[1,4]diazepane-2,5-dione The title compound was obtained in comparable yields according to the procedures described for example 1 using 1-aminomethyl-2-ethoxy-naphthaline instead of bis-3,5-trifluoromethyl-benzylamine in step a) and tert-butoxycarbonyl-DL-3,4-dichlorophenylalanine instead of tert-butoxycarbonyl-L-3,4-dichlorophenylalanine in step b).

MS m/e (%): 470.2 (M+H$^+$, 100).

EXAMPLE 18

(RS)-1-(3,5-Bis-trifluoromethyl-benzyl)-3-(2,4,5-trichloro-benzyl)-[1,4]diazepane-2,5-dione The title compound was obtained in comparable yields according to the procedures described for example 1 using tert-butoxycarbonyl-DL-2,4,5-trichlorophenylalanine instead of tert-butoxycarbonyl-L-3,4-dichlorophenylalanine in step b).

MS m/e (%): 547.1 (M+H$^+$, 100).

EXAMPLE 19

(4S)-4-(3,4-Dichloro-benzyl)-6-(2-methoxy-naphthalen-1-yl-methyl)-7,8-dihydro-6H-1,2,3a,6-tetraaza-azulen-5-one To a suspension of 107 mg (0.25 mmol) (3S)-3-(3,4-dichloro-benzyl)-1-(2-methoxy-naphthalen-1-yl-methyl)-[1,4]diazepane-2,5-dione in 2 ml dimethylformamide 20 mg (0.5 mmol) of a 55% sodium hydride suspension in mineral oil was added at room temperature under argon. After a clear solution was formed (within about 20 min) 85 mg (0.5 mmol) of bis(dimethylamino)phosphorochloridate was added. The reaction mixture was stirred at room temperature under argon for 3 hours. Formylhydrazine (60 mg, 1 mmol) was added and stirring was continued at 130° C. overnight. After evaporation of the solvent in vacuum sodium bicarbonate solution (5 ml) was added and the mixture was extracted three times with ethyl acetate. The combined organic layers are dried (MgSO$_4$) and concentrated. The residue was purified by column chromatography (SiO$_2$, dichloromethane/methanol) to yield 50 mg (44.2%) of the title compound as white crystals.

MS m/e (%): 481.3 (M+H$^+$, 100).

EXAMPLE 20

(RS)-6-(3,5-Bis-trifluoromethyl-benzyl)-4-(3,4-dichloro-benzyl)-7,8-dihydro-6H-1,2,3a,6-tetraaza-azulen-5-one The title compound was obtained in comparable yields according to the procedures described for example 19 using (RS)-1-(3,5-bis-trifluoromethyl-benzyl)-3-(3,4-dichloro-benzyl)-[1,4]diazepane-2,5-dione instead of (3S)-3-(3,4-dichloro-benzyl)-1-(2-methoxy-naphthalen-1-ylmethyl)-[1,4]diazepane-2,5-dione.

MS m/e (%): 535.9 (M+H$^+$, 100).

EXAMPLE 21

(RS)-6-(3,5-Bis-trifluoromethyl-benzyl)-4-(3,4-dichloro-benzyl)-3-(2-morpholin-4-yl-ethyl)-7,8-dihydro-6H-1,2,3a,6-tetraaza-azulen-5-one (RS)-1-(3,5-Bis-trifluoromethyl-benzyl)-3-(3,4-dichloro-benzyl)-5-thioxo-[1,4]diazepan-2-one To a suspension of 2.56 g (5 mmol) (RS)-1-(3,5-bis-trifluoromethyl-benzyl)-3-(3,4-dichloro-benzyl)-[1,4]diazepane-2,5-dione in 20 ml toluene 1.01 g (0.25 mmol) of Lawesson's reagent was added and the mixture was stirred for 2 hours at 120° C.

Water (20 ml) was added and the mixture was extracted three times with ethyl acetate. The combined organic layers are dried (MgSO$_4$) and concentrated to give a white solid. This material was purified and separated from the dithioamide by column chromatography (SiO$_2$, hexane/ethyl acetate) to yield 1.09 g (41%) of the title compound. MS m/e (%): 527.1 (M-H$^+$, 100).

(RS)-6-(3,5-Bis-trifluoromethyl-benzyl)-4-(3,4-dichloro-benzyl)-3-(2-morpholin-4-yl-ethyl)-7,8-dihydro-6H-1,2,3a,6-tetraaza-azulen-5-one To a solution of 106 mg (0.2 mmol) (RS)-1-(3,5-bis-trifluoromethyl-benzyl)-3-(3,4-dichloro-benzyl)-5-thioxo-[1,4]diazepan-2-one in 1 ml of butan-1-ol 42 mg (0.24 mmol) of 3-morpholin-4-yl-propionic acid hydrazide was added. The reaction mixture was stirred at 130° C. overnight. After evaporation of the solvent in vacuum water (5 ml) was added and the mixture was extracted three times with ethyl acetate. The combined organic layers are dried (MgSO$_4$) and concentrated. The residue was purified by column chromatography (SiO$_2$, dichloromethane/methanol= 95:5) to yield 77 mg (59.2%) of the title compound as a light yellow solid. MS m/e (%): 650.0 (M+H$^+$, 100).

EXAMPLE 22

(RS)-6-(3,5-Bis-trifluoromethyl-benzyl)-4-(3,4-dichloro-benzyl)-3-piperidin-1-yl-methyl-7,8-dihydro-6H-1,2,3a,6-tetraaza-azulen-5-one The title compound was obtained in comparable yields according to the procedures described for example 21 using piperidin-1-yl-acetic acid hydrazide instead of 3-morpholin-4-yl-propionic acid hydrazide in step b).

MS m/e (%): 634.1 (M+H$^+$, 100).

EXAMPLE 23

(RS)-6-(3,5-Bis-trifluoromethyl-benzyl)-4-(3,4-dichloro-benzyl)-3-dimethylaminomethyl-7,8-dihydro-6H-1,2,3a,6-tetraaza-azulen-5-one The title compound was obtained in comparable yields according to the procedures described for example 21 using 2-(dimethylamino)acetohydrazide instead of 3-morpholin-4-yl-propionic acid hydrazide in step b).

MS m/e (%): 594.1 (M+H$^+$, 100).

EXAMPLE 24

(RS)-6-(3,5-Bis-trifluoromethyl-benzyl)-4-(3,4-dichloro-benzyl)-3-(1-methyl-piperidin-2-yl)-7,8-dihydro-6H-1,2,3a,6-tetraaza-azulen-5-one The title compound was obtained in comparable yields according to the procedures described for example 21 using 1-methyl-piperidine-2-carboxylic acid hydrazide instead of 3-morpholin-4-yl-propionic acid hydrazide in step b).

MS m/e (%): 634.1 (M+H+, 100).

EXAMPLE 25

(RS)-4-(3,4-Dichloro-benzyl)-6-naphthalen-1-yl-methyl-7,8-dihydro-6H-1,2,3a,6-tetraaza-azulen-5-one The title compound was obtained in comparable yields according to the procedures described for example 19 using (RS)-3-(3,4-dichloro-benzyl)-1-(naphthalen-1-ylmethyl)-[1,4]diazepane-2,5-dione instead of (3S)-3-(3,4-dichloro-benzyl)-1-(2-methoxy-naphthalen-1-ylmethyl)-[1,4]diazepane-2,5-dione.

MS m/e (%): 451.3 (M+H+, 100).

EXAMPLE 26

(RS)-1-(3,5-Bis-trifluoromethyl-benzyl)-3-(3,4-dichloro-benzyl)-5-propylimino-[1,4]diazepan-2-one hydrochloride To a suspension of 160 mg (0.31 mmol) (RS)-1-(3,5-bis-trifluoromethyl-benzyl)-3-(3,4-dichloro-benzyl)-5-thioxo-[1,4]diazepan-2-one in 2 ml dimethylformamide 25 mg (0.6 mmol) of a 55% sodium hydride suspension in mineral oil was added at room temperature under argon. After a clear solution was formed (within about 20 min) 106 mg (0.62 mmol) of bis(dimethylamino)phosphorochloridate was added. The reaction mixture was stirred at room temperature under argon for 3 hours. Propylamine (91 mg, 1.25 mmol) was added and stirring was continued at 50° C. overnight. After evaporation of the solvent in vacuum sodium bicarbonate solution (5 ml) was added and the mixture was extracted three times with ethyl acetate. The combined organic layers are dried (MgSO4) and concentrated. The residue was purified by column chromatography (SiO2, dichloromethane/methanol=95:5) and converted into the hydrochloride salt using HCl in ethanol to yield 56 mg (30%) of the title compound as white crystals.

MS m/e (%): 554.1 (M+H+, 100).

EXAMPLE 27

(RS)-3-(3,4-Dichloro-benzyl)-5-(2-dimethylamino-ethylimino)-1-naphthalen-1-yl-methyl-[1,4]diazepan-2-one The title compound was obtained in comparable yields according to the procedures described for example 26 using 2-dimethylamino-ethylamine instead of propylamine.

MS m/e (%): 497.2 (M+H+, 100).

EXAMPLE 28

(3S)-1-(3,5-Bis-trifluoromethyl-benzyl)-3-(3,4-dichloro-benzyl)-4-pyridin-4-yl-methyl-[1,4]diazepane-2,5-dione S-3-[[2-Amino-3-(3,4-dichloro-phenyl)-propionyl]-(3,5-bis-trifluoromethyl-benzyl)-amino]-propionic acid tert-butyl ester To a solution of 4.56 g (10 mmol) 9-fluorenylmethoxycarbonyl-L-3,4-dichlorophenyl-alanine in 50 ml of dichloromethane 2.02 g (20 mmol) N-methylmorpholine and 2.55 g (10 mmol) bis(2-oxo-3-oxazolidinyl)phosphinic chloride were added and the mixture was stirred for 15 min at room temperature under argon. Then 3.71 g (10 mmol) 3-(3,5-bis-trifluoromethyl-benzylamino)-propionic acid tert-butyl ester (see example 1 step a) was added and the mixture was stirred for 2 h at room temperature. Water (50 ml) was added, the organic layer was separated and the aqueous layer was extracted two times with dichloromethane. The combined organic layers were dried and evaporated and the residue was purified by column filtration (SiO2, hexane/ethyl acetate=2:1). To dimethylformamide, 10 ml of diethylamine were added and the mixture was stirred for 3 h at room temperature. Dimethylformamide and diethylamine were evaporated in vacuum and the residue was purified by column chromatography (SiO2, ethyl acetate/ammonia=99.5:0.5) to give 4.82 g (82%) of the title compound as a colorless oil.

MS m/e (%): 588.4 (M+H+, 100).

(3S)-1-(3,5-Bis-trifluoromethyl-benzyl)-3-(3,4-dichloro-benzyl)-4-pyridin-4-yl-methyl-[1,4]diazepane-2,5-dione To a solution of 393 mg (0.67 mmol) S-3-[[2-amino-3-(3,4-dichloro-phenyl)-propionyl]-(3,5-bis-trifluoromethyl-benzyl)-amino]-propionic acid tert-butyl ester in 1,2-dichloroethane 71.7 mg (0.67 mmol) of 4-pyridine carboxyaldehyde, 80.4 mg (1.34 mmol) of acetic acid and 198 mg (0.94 mmol) of sodium triacetoxyborohydride were added and the mixture was stirred at room temperature overnight. Sodium bicarbonate solution (5 ml) was added and the mixture was extracted three times with dichloromethane. The combined organic layers are dried (MgSO4) and concentrated to give 370 mg of a yellow oil which was dissolved in a mixture of dichloromethane (1 ml) and trifluoroacetic acid (1 ml). The reaction mixture was stirred for 2 hours at room temperature. The solvent and the trifluoroacetic acid were evaporated at reduced pressure. After drying under vacuum the residue was dissolved in 5 ml of dichloromethane and 220 mg (2.18 mmol) N-methylmorpholine, 105 mg (0.55 mmol) N-(3-dimethylaminopropyl)-N'-ethylcarbodiimide hydrochloride and 74 mg (0.55 mmol) 1-hydroxybenzotriazole were added. The mixture was stirred overnight at room temperature. Water (5 ml) was added to the reaction mixture, the two phases were separated and the organic layer was dried over magnesium sulphate. After evaporation of the solvent the residue was purified by column chromatography (SiO2, dichloromethane/methanol=95:5) to give 158 mg (48%) of the title compound as a white solid.

MS m/e (%): 603.9 (M+H+, 100).

EXAMPLE 29

(RS)-3-(3,4-Dichloro-benzyl)-1-(2-methoxy-naphthalen-1-yl-methyl)-4-pyridin-3-yl-methyl-[1,4]diazepane-2,5-dione The title compound was obtained in comparable yields according to the procedures described for example 28 using 9-fluorenylmethoxycarbonyl-DL-3,4-dichlorophenyl-alanine instead of 9-fluorenylmethoxycarbonyl-L-3,4-dichlorophenylalanine and 3-[(2-methoxy-naphthalen-1-ylmethyl)-amino]-propionic acid tert-butyl ester instead of 3-(3,5-bis-trifluoromethyl-benzylamino)-propionic acid tert-butyl ester in step a) and 3-pyridine carboxyaldehyde instead of 4-pyridine carboxyaldehyde in step b).

MS m/e (%): 548.1 (M+H+, 100).

EXAMPLE 30

(RS)-1-(3,5-Bis-trifluoromethyl-benzyl)-3-(3,4-dichloro-benzyl)-4-(1-methyl-piperidin-4-yl)-[1,4]diazepane-2,5-dione The title compound was obtained in comparable yields according to the procedures described for example 28 using 9-fluorenylmethoxycarbonyl-DL-3,4-dichlorophenyl-alanine instead of 9-fluorenylmethoxycarbonyl-L-3,4-dichlorophenylalanine in step a) and 1-methyl-4-piperidone instead of 4-pyridine carboxyaldehyde in step b).

MS m/e (%): 610.0 (M+H$^+$, 100).

EXAMPLE 31

(3S)-1-(3,5-Bis-trifluoromethyl-benzyl)-3-(3,4-dichloro-benzyl)-4-pyridin-2-yl-methyl-[1,4]diazepane-2,5-dione The title compound was obtained in comparable yields according to the procedures described for example 28 using 2-pyridine carboxyaldehyde instead of 4-pyridine carboxyaldehyde in step b).

MS m/e (%): 603.9 (M+H$^+$, 100).

EXAMPLE 32

(RS)-1-(3,5-Bis-trifluoromethyl-benzyl)-3-(3,4-dichloro-benzyl)-4-pyridin-4-yl-methyl-[1,4]diazepane-2,5-dione The title compound was obtained in comparable yields according to the procedures described for example 28 using 9-fluorenylmethoxycarbonyl-DL-3,4-dichlorophenyl-alanine instead of 9-fluorenylmethoxycarbonyl-L-3,4-dichlorophenylalanine in step a).

MS m/e (%): 603.9 (M+H$^+$, 100).

EXAMPLE 33

(RS)-1-(3,5-Bis-trifluoromethyl-benzyl)-3-(3,4-dichloro-benzyl)-4-pyridin-3-yl-methyl-[1,4]diazepane-2,5-dione The title compound was obtained in comparable yields according to the procedures described for example 28 using 9-fluorenylmethoxycarbonyl-DL-3,4-dichlorophenyl-alanine instead of 9-fluorenylmethoxycarbonyl-L-3,4-dichlorophenylalanine in step a) and 3-pyridine carboxyaldehyde instead of 4-pyridine carboxyaldehyde in step b).

MS m/e (%): 603.9 (M+H$^+$, 100).

EXAMPLE 34

(3S)-1-(3,5-Bis-trifluoromethyl-benzyl)-3-(3,4-dichloro-benzyl)-4-(1H-pyrazol-3-yl-methyl)-[1,4]diazepane-2,5-dione The title compound was obtained in comparable yields according to the procedures described for example 28 using pyrazole-3-carbaldehyde instead of 4-pyridine carboxyaldehyde in step b).

MS m/e (%): 593.0 (M+H$^+$, 100).

EXAMPLE 35

(3S)-1-(3,5-Bis-trifluoromethyl-benzyl)-3-(3,4-dichloro-benzyl)-4-(2-dimethylamino-ethyl)-[1,4]diazepane-2,5-dione; hydrochloride The title compound was obtained in comparable yields according to the procedures described for example 28 using 2-dimethylaminoacetaldeyde instead of 4-pyridine carboxyaldehyde in step b) and subsequent formation of the hydrochloride salt using HCl in ethanol.

MS m/e (%): 584.1 (M+H$^+$, 100).

EXAMPLE 36

(RS)-3-(3,4-Dichloro-benzyl)-1-(3,4,5-trimethoxy-benzyl)-[1,4]diazepane-2,5-dione The title compound was obtained in comparable yields according to the procedures described for example 1 using 3,4,5-trimethoxy-benzylamine instead of bis-3,5-trifluoromethyl-benzylamine in step a) and tert-butoxycarbonyl-DL-3,4-dichlorophenylalanine instead of tert-butoxycarbonyl-L-3,4-dichlorophenylalanine in step b).

MS m/e (%): 466.1 (M+H$^+$, 15), 181.1 (100).

EXAMPLE A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the structure:

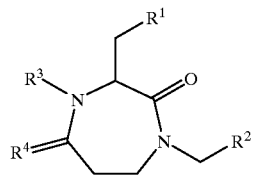

wherein
- $R^1$ and $R^2$, are a substituted or unsubstituted phenyl or napthyl ring, or a substituted or unsubstituted heteroaryl ring selected from the group consisting of pyridyl, pyrazinyl, pyrimidinyl, pyridazinyl, indazolyl, indolyl, pyrazolyl, benzothienyl, thienyl, furyl, pyrrolyl, imidazolyl, isoquinolyl, isothiazolyl and quinolinyl, said substituted phenyl, naphthyl or heteroaryl ring being substituted with one to three substituents selected from the group consisting of halogeng, $CF_3$, lower alkoxy, and lower alkyl;
- $R^3$ is independently hydrogen, lower alkyl, $-(CH_2)_nN(R)_2$, $-(CH_2)_n-X-$;
- $R^4$ is independently $=O$, $=N(CH2)_nCH3$ or $=N(CH_2)_nNR_2$, or taken together with $R^3$ and with their respective attached N and C atoms form $-CR^5=N-N=$;
- $R^5$ is hydrogen, $-(CH_2)_nN(R)_2$ or is a substituted or unsubstituted $-(CH_2)_n-X$;
- X is a substituted or unsubstituted heterocyclic ring selected from the group consisting of morpholinyl, piperidinyl, pyrrolidinyl, imidazolidinyl, pyrazolidinyl, piperidyl and piperazinyl, said substituted heterocyclic ring being substituted with one to three substituents selected from the group consisting of halogen, $CF_3$, lower alkoxy, and lower alkyl;
- R is hydrogen or lower alkyl; and
- n is 0, 1, 2 or 3; or a pharmaceutically acceptable salt or an enantiomeric forms thereof.

2. The compound of claim 1 having the structure

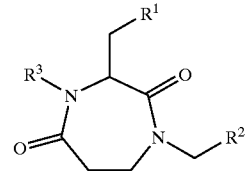

wherein are $R^1$ and $R^2$ as defined above.

3. The compound of claim 2 wherein $R^3$ is H.

4. The compound of claim 3 wherein $R^1$ is an unsubstituted or substituted phenyl ring.

5. The compound of claim 4 wherein said $R^1$ is a substituted phenyl ring.

6. The compound of claim 5 wherein the compound is (3S)-1-(3,5-bis-trifluoromethyl-benzyl)-3-(3,4-dichloro-benzyl)-[1,4]diazepane-2,5-dione.

7. The compound of claim 5 wherein the compound is (3S)-1(RS)-1-(3,5-bis-trifluoromethyl-benzyl)-3-(2,4,5-trichloro-benzyl)-[1,4]diazepane-2,5-dione.

8. The compound of claim 5 wherein the compound is (RS)-3-(3,4-dichloro-benzyl)-1-(3,4,5-trimethoxy-benzyl)-[1,4]diazepane-2,5-dione.

9. The compound of claim 4 wherein $R^2$ is an unsubstituted napthyl ring.

10. The compound of claim 9 wherein the compound is (RS)-3-(3,4-dichloro-benzyl)-1-naphthalen-1-yl-methyl-[1,4]diazepane-2,5-dione.

11. The compound of claim 9 wherein the compound is (3S)-3-(3,4-dichloro-benzyl)-1-naphthalen-1-yl-methyl-[1,4]diazepane-2,5-dione.

12. The compound of claim 9 wherein the compound is (3S)-3-(4-chloro-benzyl)-1-naphthalen-1-yl-methyl-[1,4]diazepane-2,5-dione.

13. The compound of claim 9 wherein the compound is (3S)-3-(3-chloro-benzyl)-1-naphthalen-1-yl-methyl-[1,4]diazepane-2,5-dione.

14. The compound of claim 5 wherein $R^2$ is a substituted napthyl ring.

15. The compound of claim 14 wherein the compound is (3S)-3-(3,4-dichloro-benzyl)-1-(2-methoxy-naphthalen-1-yl-methyl)-[1,4]diazepane-2,5-dione.

16. The compound of claim 14 wherein the compound is (3S)-3-(3,4-dichloro-benzyl)-1-(2-methyl-naphthalen-1-yl-methyl)-[1,4]diazepane-2,5-dione.

17. The compound of claim 14 wherein the compound is (RS)-3-(3,4-dichloro-benzyl)-1-(2-ethoxy-naphthalen-1-yl-methyl)-[1,4]diazepane-2,5-dione.

18. The compound of claim 3 wherein $R^1$ is a heteroaromatic ring selected from the group consisting of pyridyl, pyrazinyl, pyrimidinyl, pyridazinyl, indazolyl, indolyl, pyrazolyl, benzothienyl, thienyl, furyl, pyrrolyl, imidazolyl, isoquinolyl, isothiazolyl, and quinolinyl.

19. The compound of claim 18 wherein $R^2$ is a substituted phenyl ring.

20. The compound of claim 19 wherein the compound is (3S)-1-(3,5-bis-trifluoromethyl-benzyl)-3-(1H-indol-3-yl-methyl)-[1,4]diazepane-2,5-dione.

21. The compound of claim 19 wherein the compound is (3S)-1-(4-chloro-3-trifluoromethyl-benzyl)-3-(1H-indol-3-yl-methyl)-[1,4]diazepane-2,5-dione.

22. The compound of claim 18 wherein $R^2$ is an unsubstituted napthyl ring structure.

23. The compound of claim 22 wherein the compound is (3S)-3-(1H-indol-3-yl-methyl)-1-naphthalen-1-yl-methyl-[1,4]diazepane-2,5-dione.

24. The compound of claim 22 wherein the compound is (3S)-3-benzo[b]thiophen-3-yl-methyl-1-naphthalen-1-yl-methyl-[1,4]diazepane-2,5-dione.

25. The compound of claim 18 wherein $R^2$ is a substituted napthyl ring.

26. The compound of claim 25 wherein the compound is (3S)-3-(1H-indol-3-yl-methyl)-1-(2-methoxy-naphthalen-1-yl-methyl)-[1,4]diazepane-2,5-dione.

27. The compound of claim 25 wherein the compound is (3S)-3-(1H-indol-3-yl-methyl)-1-(4-methoxy-naphthalen-1-yl-methyl)- [1,4]diazepane-2,5-dione.

28. The compound of claim 18 wherein $R^2$ is a heteroaromatic ring selected from the group consisting of pyridyl, pyrazinyl, pyrimidinyl, pyridazinyl, indazolyl, indolyl, pyrazolyl, benzothienyl, thienyl, furyl, pyrrolyl, imidazolyl, isoquinolyl, isothiazolyl, and quinolinyl.

29. The compound of claim 28 wherein the compound is (3S)-1-(2,8-bis-trifluoromethyl-quinolin-4-yl-methyl)-3-(1H-indol-3-yl-methyl)-[1,4]diazepane-2,5-dione.

30. The compound of claim 2 wherein $R^3$ is a heterocyclic ring selected from the group consisting of morpholinyl, piperidinyl, pyrrolidinyl, imidazolidinyl, pyrazolidinyl, piperidyl and piperazinyl.

31. The compound of claim 30 wherein $R^1$ and $R^2$ are substituted and unsubstituted phenyl and napthyl rings.

32. The compound of claim 31 wherein the compound is (RS)-3-(3,4-dichloro-benzyl)-4-(2-morpholin-4-yl-ethyl)-1-naphthalen-1-yl-methyl-[1,4]diazepane -2,5-dione hydrochloride.

33. The compound of claim 31 wherein the compound is (RS)-1-(3,5-bis-trifluoromethyl-benzyl)-3-(3,4-dichloro-benzyl)-4-(1-methyl-piperidin-4-yl)-[1,4]diazepane-2,5-dione.

34. The compound of claim 2 wherein $R^1$ and $R^2$ are substituted or unsubstituted phenyl or napthyl rings.

35. The compound of claim 34 wherein $R^3$ is an aromatic heterocycle selected from the group consisting of pyridyl, pyrazinyl, pyrimidinyl, pyridazinyl, indazolyl, indolyl, pyrazolyl, benzothienyl, thienyl, furyl, pyrrolyl, imidazolyl, isoquinolyl, isothiazolyl, and quinolinyl.

36. The compound of claim 35 wherein the compound is (3S)-1-(3,5-bis-trifluoromethyl-benzyl)-3-(3,4-dichloro-benzyl)-4-pyridin-4-yl-methyl-[1,4]diazepane-2,5-dione.

37. The compound of claim 35 wherein the compound is (RS)-3-(3,4-dichloro-benzyl)-1-(2-methoxy-naphthalen-1-yl-methyl)-4-pyridin-3-yl-methyl -[1,4]diazepane-2,5-dione.

38. The compound of claim 35 wherein the compound is (3S)-1-(3,5-bis-trifluoromethyl-benzyl)-3-(3,4-dichloro-benzyl)-4-pyridin-2-yl-methyl -[1,4]diazepane-2,5-dione.

39. The compound of claim 35 wherein the compound is (RS)-1-(3,5-bis-trifluoromethyl-benzyl)-3-(3,4-dichloro-benzyl)-4-pyridin-4-yl-methyl -[1,4]diazepane-2,5-dione.

40. The compound of claim 35 wherein the compound is (RS)-1-(3,5-bis-trifluoromethyl-benzyl)-3-(3,4-dichloro-benzyl)-4-pyridin-3-yl-methyl -[1,4]diazepane-2,5-dione.

41. The compound of claim 35 wherein the compound is (3S)-1-(3,5-bis-trifluoromethyl-benzyl)-3-(3,4-dichloro-benzyl)-4-(1H-pyrazol-3-yl-methyl) -[1,4]diazepane-2,5-dione.

42. The compound of claim 2 wherein $R^3$ is —$(CH_2)_n$N$(R)_2$.

43. The compound of claim 42 wherein the compound is (3S)-1-(3,5-bis-trifluoromethyl-benzyl)-3-(3,4-dichloro-benzyl)-4-(2-dimethylamino-ethyl) -[1,4]diazepane-2,5-dione; hydrochloride.

44. The compound of claim 2 wherein $R^3$ is lower alkyl.

45. The compound of claim 44 wherein $R^1$ and $R^2$ are substituted or unsubstituted phenyl or napthyl rings.

46. The compound of claim 45 wherein the compound is (RS)-3-(3,4-dichloro-benzyl)-4-methyl-1-naphthalen-1-yl-methyl-[1,4]diazepane-2,5-dione.

47. The compound of claim 1 having the structure

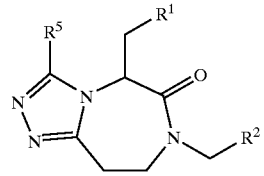

1-b wherein $R^1$ and $R^2$ are substituted or unsubstituted phenyl or napthyl rings.

48. The compound of claim 47 wherein $R^5$ is hydrogen.

49. The compound of claim 48 wherein the compound is (RS)-6-(3,5-bis-trifluoromethyl-benzyl)-4-(3,4-dichloro-benzyl)-7,8-dihydro-6H-1,2,3a,6-tetraaza-azulen-5-one.

50. The compound of claim 49 wherein the compound is (4S)-4-(3,4-dichloro-benzyl)-6-(2-methoxy-naphthalen-1-yl-methyl)-7,8-dihydro-6H-1,2,3a,6-tetraaza-azulen-5-one.

51. The compound of claim 48 wherein the compound is (RS)-4-(3,4-dichloro-benzyl)-6-naphthalen-1-yl-methyl-7,8-dihydro-6H-1,2,3a,6-tetraaza-azulen-5-one.

52. The compound of claim 47 wherein $R^5$ is a non-aromatic heterocyclic ring selected from the group consisting of morpholinyl, piperidinyl, pyrrolidinyl, imidazolidinyl, pyrazolidinyl, piperidyl and piperazinyl.

53. The compound of claim 52 wherein $R^1$ and $R^2$ are substituted or unsubstituted phenyl or napthyl ring.

54. The compound of claim 53 wherein the compound is (RS)-6-(3,5-bis-trifluoromethyl-benzyl)-4-(3,4-dichloro-benzyl)-3-(2-morpholin-4-yl-ethyl) -7,8-dihydro-6H-1,2,3a,6-tetraaza-azulen-5-one.

55. The compound of claim 53 wherein the compound is (RS)-6-(3,5-bis-trifluoromethyl-benzyl)-4-(3,4-dichloro-benzyl)-3-piperidin-1-yl-methyl-7,8-dihydro -6H-1,2,3a,6-tetraaza-azulen-5-one.

56. The compound of claim 53 wherein the compound is (RS)-6-(3,5-bis-trifluoromethyl-benzyl)-4-(3,4-dichloro-benzyl)-3-(1-methyl-piperidin-2-yl)-7,8-dihydro-6H-1,2,3a,6-tetraaza-azulen-5-one.

57. The compound of claim 47 wherein $R^5$ is amino alkyl.

58. The compound of claim 57 wherein the compound is (RS)-6-(3,5-bis-trifluoromethyl-benzyl)-4-(3,4-dichloro-benzyl)-3-dimethylaminomethyl-7,8-dihydro-6H-1,2,3a,6-tetraaza-azulen-5-one.

59. The compound of claim 1 having the structure

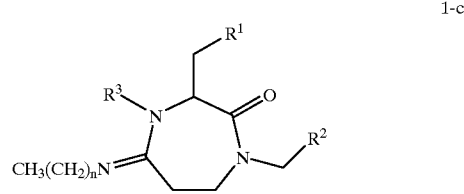

1-c wherein $R^3$ is hydrogen, $R^4$ is =$N(CH_2)_n$R, and $R^1$ and $R^2$ are substituted or unsubstituted phenyl or napthyl rings.

60. The compound of claim 59 wherein the compound is (RS)-1-(3,5-bis-trifluoromethyl-benzyl)-3-(3,4-dichloro-benzyl)-5-propylimino-[1,4]diazepan-2-one hydrochloride.

61. The compound of claim 59 wherein the compound is (RS)-3-(3,4-dichloro-benzyl)-5-(2-dimethylamino-ethylimino)-1-naphthalen-1-yl-methyl-[1,4]diazepan-2

* * * * *